United States Patent
Venkateswaran

(10) Patent No.: US 6,258,344 B1
(45) Date of Patent: Jul. 10, 2001

(54) SKIN LIGHTENING COMPOSITIONS

(75) Inventor: Ananthanarayan Venkateswaran, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/202,873

(22) PCT Filed: Jul. 2, 1996

(86) PCT No.: PCT/US96/11211

§ 371 Date: Dec. 22, 1998

§ 102(e) Date: Dec. 22, 1998

(87) PCT Pub. No.: WO98/00106

PCT Pub. Date: Jan. 8, 1998

(51) Int. Cl.$^7$ .................. A61K 7/00; A61K 7/135
(52) U.S. Cl. .......................... 424/62; 424/401
(58) Field of Search ................. 424/62, 78.03, 424/401; 514/937, 944, 947, 969

(56) References Cited

U.S. PATENT DOCUMENTS

| | | | |
|---|---|---|---|
| 3,989,816 | 11/1976 | Rhaadhyaksha | 424/88 |
| 4,017,641 | 4/1977 | DiGiulio | 424/365 |
| 4,130,667 | 12/1978 | Smith | 424/361 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,954,487 | 9/1990 | Cooper et al. | 514/159 |
| 5,198,210 | * 3/1993 | Critchley et al. | 424/78.03 |
| 5,216,033 | 6/1993 | Pereira et al. | 514/844 |

FOREIGN PATENT DOCUMENTS

| | | | |
|---|---|---|---|
| 2 079 300 | 1/1982 | (GB) | C08L/83/04 |
| WO 95/23780 | * 9/1995 | (WO) | |
| WO 96/14055 | 5/1996 | (WO) | A61K/7/48 |

OTHER PUBLICATIONS

Cooper, E.R., "Effect of Decylmethylsulfoxide on Skin Penetration", Solution Behavior of Surfactants, vol. 2, Mitta/Fendler, Eds), Plenum Publishing Corp, pp. 1505–1516 (1982).

Mahjour, M.B., et al., "Effect of Egg Yolk Lecithins and Commercial Soybean Lecithins on In Vitro Skin Permeation of Drugs", Journal of Controlled Release, vol. 14, pp. 243–252 (1990).

Williams, A.C., et al., "Terpenes and the Lipid–Protein–Partitioning Theory of Skin Penetration Enhancement", Pharmaceutical Research, vol. 8, No. 1, pp. 17–24 (1991).

Wong., O., et al., "New Alkyl N,N–Dialkyl–Substituted Amino Acetates as Transdermal Penetration Enhancers", Pharmaceutical Research, vol. 6, No. 4, pp. 286–295 (1989).

Wong, O., et al., "Unsaturated Cyclic Ureas as New Nontoxic Biodegradable Transdermal Penetration Enhancers I: Synthesis", Journal of Pharmaceutical Sciences, vol. 77, No. 11, pp. 967–971 (Nov. 1988).

* cited by examiner

*Primary Examiner*—Thurman K. Page
*Assistant Examiner*—S. Howard
(74) *Attorney, Agent, or Firm*—Dara M. Kendall; Fumiko Tsuneki; Michael E. Hilton

(57) ABSTRACT

The subject invention relates to a water-in-silicone gel composition for skin lightening comprising: a) a safe and effective amount of a compound of formula (I), wherein Z is oxygen or sulfur; b) a mixture of dimethicone copolyol surfactant and cyclomethicone; and c) a cosmetically-acceptable carrier for said compound of formula (I) and said mixture.

(I)

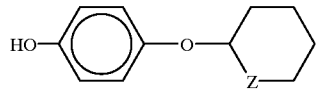

16 Claims, No Drawings

SKIN LIGHTENING COMPOSITIONS

TECHNICAL FIELD

The subject invention relates to the field of skin lightening. Specifically, the subject invention relates to novel water-in-silicone gel compositions which enhance skin penetration effect of specific hydroquinone derivatives for skin lightening.

BACKGROUND OF THE INVENTION

The specific hydroquinone as shown in formula (I) is known as a skin lightening compound. See WO9523780.

formula (I)

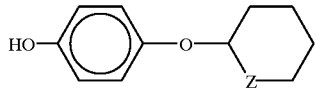

wherein Z is oxygen or sulfur.

The combination of the specific hydroquinone derivatives and penetration enhancers is disclosed in WO9523780.

WO9523780 describes that penetration enhancers are disclosed in U.S. Pat. No. 4,537,776, Cooper, issued Aug. 27, 1985; U.S. Pat. No. 4,552,872, Cooper et al., issued Nov. 12, 1985; U.S. Pat. No. 4,557,934, Cooper, issued Dec. 10, 1985; U.S. Pat. No. 4,130,667, Smith, issued Dec. 19, 1978; U.S. Pat. No. 3,989,816, Rhaadhyaksha, issued Nov. 2, 1976; U.S. Pat. No. 4,017,641, DiGiulio, issued Apr. 12, 1977; and U.S. Pat. No. 4,954,487, Cooper, Loomans & Wickett, issued Sep. 4, 1990, and additional penetration enhancers are disclosed in Cooper, E. R., "Effect of Decylmethylsulfoxide on Skin Penetration", *Solution Behavior of Surfactants*, Vol. 2 (Mittal and Fendler, eds.), Plenum Publishing Corp., 1982, pp. 1505–1516; Mahjour, M., B. Mauser, Z. Rashidbaigi & M. B. Fawzi, "Effect of Egg Yolk Lecithins and Commercial Soybean Lecithins on In Vitro Skin Permeation of Drugs", *Journal of Controlled Release*, Vol. 14 (1990), pp. 243–252; Wong, O., J. Huntington, R. Konishi, J. H. Rytting & T. Higuchi, "Unsaturated Cyclic Ureas as New Nontoxic Biodegradable Transdermal Penetration Enhancers I: Synthesis", *Journal of Pharmaceutical Sciences*, Vol. 77, No. 11 (November 1988), pp. 967–971; Williams, A. C. & B. W. Barry, "Terpenes and the Lipid-Protein-Partitioning Theory of Skin Penetration Enhancement", *Pharmaceutical Research*, Vol. 8, No. 1 (1991), pp. 17–24; and Wong, O., J. Huntington, T. Nishihata & J. H. Rytting, "New Alkyl N,N-Dialkyl-Substituted Amino Acetates as Transdermal Penetration Enhancers", *Pharmaceutical Research*, Vol. 6, No. 4 (1989), pp. 286–295.

Water-in-silicone composition are disclosed in GB patent publication No. 2079300A and U.S. Pat. No. 5,216,033A, but there are no description of the combination of the specific hydroquinone derivatives of formula(I) and the water-in-silicone composition, which works for enhancing penetration.

It is an object of the present invention to provide compositions for lightening mammalian skin which has a good penetration effect, so that the specific hydroquinone derivatives which are skin lightening actives can penetrate effectively and work effectively.

SUMMARY OF THE INVENTION

The subject invention relates to a water-in-silicone gel composition for skin lightening comprising (a) a safe and effective amount of a compound of the formula (I) formula (I):

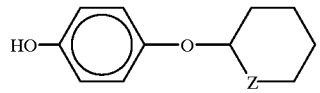

wherein Z is oxygen or sulfur, (b) a mixture of dimethicone copolyol surfactant and cyclomethicone (c) a cosmetically-acceptable carrier for said compound of formula(I) and said mixture.

DETAILED DESCRIPTION OF THE INVENTION

The compound of the formula(I) have a good skin lightening effect in mammals, however it is expected to strengthen the penetration effect of the compound of formula (I) to mammal's skin. It has been unexpectedly found that the subject composition achieve good penetration in mammal's skin of the compounds of formula (I).

In order to achieve a good penetration effect, the composition of the present invention must form a water-in-silicone gel.

As used herein, "topical application" means directly laying on or spreading on outer skin.

As used herein, "skin lightening" means decreasing melanin in skin, including one or more of overall lightening of basal skin tone, lightening of hyperpigmented lesions including age spots, melasma, chloasma, freckles, post inflammatory hyperpigmentation or sun-induced pigmented blemishes.

As used herein, all percentages are by weight unless otherwise specified.

As used herein, "dimethicone copolyol" means "polymer of dimethylsiloxane with polyoxyethylene and/or polyoxypropylene side chains".

As used herein "cyclomethicone" means "cyclic dimethyl polysiloxane".

The weight ratio of said compound of formula(I): the mixture of dimethicone copolyol surfactant and cyclomethicone: the cosmetically acceptable carrier should be 0.001–10:10–30:89.999–60.

The typical examples of the compound of formula(I) is as follows.

4-[(tetrahydro-2H-pyran-2-yl)oxy]phenol (hereinafter called THPOP)

4-[(tetrahydro-2H-thiopyran-2-yl)oxy]phenol.

These compounds are produced by the method described in WO9523780.

A skin lightening composition of the present invention preferably comprises from about 0.001% to about 10% of a compound of the formula(I) in a topical composition, more preferably from about 0.01% to about 8%, still more preferably from about 0.1% to about 5%, most preferably from about 0.5% to about 3% of a compound of the formula(I).

Use of subject compositions comprising over 3% of an active is preferred for lightening of hyperpigmented lesions and other areas where substantial lightening is desired.

Mixture of dimethicone copolyol surfactant and cyclomethicone

The weight ratio of dimethicone copolyol surfactant: cyclomethicone is typically 5:95–25:75, preferably 5:95–18:85, more preferably 5:95–10:90. The mixture has good effect for imparting a preferred skin feel. Generally such silicones of the mixture have a low molecular weight. The suitable mixture of dimethicone copolyol surfactant and cyclomethicone include Dow Corning Q2-3225C, which are available from the Dow Corning Corp. of Midland, Mich.

A skin lightening composition of the present invention comprises preferably from 10% to about 30%, more preferably from about 15% to about 20%, of a mixture of dimethicone copolyol surfactant and cyclomethicone.

Cosmetically Acceptable Carrier for said compound of formula(I) and said mixture The phrase "cosmetically acceptable carrier", as used herein, means one or more compatible solid or liquid fillers, diluents, extenders and the like, which are cosmetically acceptable as defined herein. The term "compatible", as used herein, means that the components of the compositions of this invention are capable of being commingled with the primary actives of the present invention, and with each other, in a manner such that there is no interaction which would substantially reduce the efficacy of the composition under ordinary use situations. The type of carrier utilized in the present invention depends on the type of product desired. The topical compositions useful in the subject invention may be made into a wide variety of product types. These include, but are not limited to, lotions, gels, sprays, ointments, and mousses. These product types may comprise several types of carriers including, but not limited to solutions, aerosols and gels.

Solutions according to the subject invention typically include a cosmetically acceptable aqueous or organic solvent which is capable of having the primary actives dispersed or dissolved therein. In order to dissolve the compound of formula(I), since the compounds of formula(I) are molecules of average polarity (the "solubility parameters" are around 9.5) being neither soluble in very polar solvents nor very non polar solvents, it is necessary to be dissolved in an average polarity solvents. The average polarity solvents could preferably be solvents which have solubility parameter of 7 to 11, more preferably be solvents which have solubility parameter of 8 to 10. The average polarity solvents include water soluble glycol ether; mono lower alcohol such as ethanol; polyhydric alcohol; triglyceride such as capric/caprylic triglyceride; neopentyl glycol dioctoanate (Trade name: Cosmol, manufactured by Nisshin Oil Mills (LTD.); octyl methoxy cinnamate; and ether of polyoxypropylene or polyoxyethylene and aliphatic alcohol such as polyoxypropylene 15 stearyl ether and polypropylene glycol-14 butyl ether.

The above mentioned water soluble ether can be characterized by the general formula: $R^1-O-[(CH_2)_mO]_nH$; wherein $R^1$ is an alkyl of 1 to 6 carbon atoms, m is from about 2 to about 3, and n is from about 1 to about 2. Examples of the alkylene/dialkylene group include ethylene, propylene and diethylene groups. Examples of the alkyl group $R^1$ include methyl, ethyl, propyl, butyl, hexyl groups. This glycol ether having a diethylene group as the alkylene group and ethyl group as the alkyl moiety is diethyleneglycol monoethyl ether which has been give the CTFA designation ethoxydiglycol. One of the most preferred is commercially available by the tradename Transcutol from Gattefosse, France.

Examples of the above mentioned polyhydric alcohol include glycerin, diglycerin, triglycerin, polyethylene glycol, ethylene glycol, diethylene glycol, propylene glycol, dipropylene glycol, hexylene glycol, 1,3-butylene glycol, 1,4-butylene glycol, glucose, maltose, sucrose, xylitose, sorbitol, maltitol, malbit, panthenol, hyaluronic acid and its salts, and mixtures thereof.

Either diethylene glycol monoethyl ether (Transcutol) or a combination of diethylene glycol monoethyl ether (Transcutol), ethanol and propylene glycol is preferred to be used as a solubilizer to keep the compounds of formula (I) in aqueous phase and a dimethicone copolyol surfactant can be used as a continuous phase to form stable clear gel. The good penetration effect is not obtained by the average polarity solvents per se but is obtained by the water-in-silicone gel.

The amount of the average polarity solvents depends on the amount of the compounds of formula (I).

Other carriers than the above average polarity solvents include water.

Aerosols composition comprising the subject invention can be formed by adding a propellant to a solution such as described above. Exemplary propellants include chlorofluorinated lower molecular weight hydrocarbons. Additional propellants that are useful herein are described in Sagarin, *Cosmetics Science and Technology*, 2nd Edition, Vol. 2, pp. 443–465 (1972), incorporated herein by reference. Aerosols are typically applied to the skin as a spray-on product.

A skin lightening composition of the present invention comprises preferably from about 60% to about 89.999%, more preferably from about 72% to about 84.99% of the cosmetically-acceptable carrier.

Preferred compositions of the present invention have a high viscosity, of from about 10,000 to about 300,000 centipoise, more preferably from about 20,000 to about 200,000 centipoise, most preferably from about 50,000 to about 150,000 centipoise.

In addition to the primary actives, ointments composition comprising the present invention may comprise a simple carrier base of hydrocarbons or water soluble carriers, e.g., a water soluble solution carrier. Ointments may further comprise a thickening agent, such as described in Sagarin, *Cosmetics, Science and Technology*, 2nd Edition, Vol. 1, pp. 72–73 (1972), incorporated herein by reference, and/or a carrier. For example, an ointment may comprise from about 2% to about 10% of carrier; from about 0.1% to about 2% of a thickening agent; and the primary actives in the above described amount.

The compositions of the present invention are preferably formulated to have a pH of 8 or above. The pH values of these compositions preferably range from about 8 to about 9, more preferably from about 8 to about 8.5, most preferably from about 8.2 to about 8.5. Compositions having a pH within the range of about 4.5 to 8.0 tend to exhibit less stability relative to corresponding compositions having a pH of greater than about 8.0.

Combination Actives

A. Sunscreens and Sunblocks

Regulation of skin darkening resulting from exposure to ultraviolent light can be achieved by using combinations of the active skin lightening agents together with sunscreens or sunblocks. Useful sunblocks include, for example, zinc oxide and titanium dioxide.

Ultraviolet light is a predominant cause of skin darkening. Thus, for purposes of skin lightening, the combination of a skin lightening agent with a UVA and/or UVB sunscreen is desirable.

A wide variety of conventional sunscreening agents are suitable for use in combination with the skin lightening agent. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); Cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphthol-sulfonates (sodium salts of 2-naphthol-3,6-disulfonic and of 2-naphthol-6,8-disulfonic acids); di-hydroxy-naphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxy-benzene, sulisobenzone, dioxybenzone, benzoresorcinol, 2,2',4,4'-tetrahydroxybenzophenone, 2,2'-dihydroxy-4,4'-dimethylbenzophenone, octabenzone; 4-isopropyldibenzoylmethane; butyl-methoxydibenzoylmethane; etocrylene; and 4-isopropyl-dibenzoylmethane.

Of these, 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxybenzoylmethane; 4-N,N-(2-ethylhexyl)methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used in the compositions useful in the subject invention. The sunscreening agent must be compatible with the skin lightening agent. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred skin lightening composition useful in the subject invention, an anti-inflammatory agent is included as an active along with the skin lightening agent. The inclusion of an anti-inflammatory agent enhances the skin lightening benefits of the compositions. The anti-inflammatory agent protects strongly in the UVA radiation range (though it also provides some UVB protection as well). The topical use of anti-inflammatory agents reduces darkening of the skin resulting from chronic exposure to UV radiation. (See U.S. Pat. No. 4,847,069, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal antiinflammatory agents. The variety of compounds encompassed by this group are well-known to those skilled in the art. For detailed disclosure of the chemical structure, synthesis, side effects, etc., of non-steroidal antiinflammatory agents, reference may be had to standard texts, including *Antiinflammatory and Anti-Rheumatic Drugs,* K. D. Rainsford, Vol I–III, CRC Press, Boca Raton, (1985), and *Anti-inflammatory Agents, Chemistry and Pharmacology,* 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(–)-3'-methyl-5'-hexynoyl)-2,6-di-t-butylphenol; 4-((R)-(+)-3'-methyl-5'-hexynoyl)-2,6-di-t-butylphenol; and 4-(3',3,'-dimethoxypropionyl)-2,6-di-t-butylphenol are useful in methods of the subject invention; 4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the subject invention.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

Another preferred composition useful in the subject invention comprises a skin lightening agent, a sunscreen, and an anti-inflammatory agent together for skin lightening in the amounts disclosed for each individually hereinabove.

C. Anti-Oxidants/Radical Scavengers

In a preferred skin lightening composition useful in the subject invention, an anti-oxidant/radical scavenger is included as an active along with the skin lightening agent. The inclusion of an anti-oxidant/radical scavenger increases the skin lightening benefits of the composition.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox☐), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred composition useful in the subject invention, compositions comprise one, any two, or all three of a sunscreening agent, anti-inflammatory agent, and/or an anti-oxidant/radical scavenging agent included as actives along with the skin lightening agent. The inclusion of two or all three of these agents with the skin lightening agent increases the skin lightening benefits of the composition.

D. Chelators

In a preferred composition useful in the subject invention, a chelating agent is included as an active along with the skin lightening agent. As used herein, "chelating agent" means an active agent capable of removing a metal ion from a system by forming a complex so that the metal ion cannot readily participate in or catalyze chemical reactions. The inclusion of a chelating agent increases the skin lightening benefits of the composition.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furildioxime and derivatives thereof.

In a preferred composition useful in the subject invention, compositions comprise one, any two, any three, or all four of a sunscreening agent, anti-inflammatory agent, anti-oxidant/radical scavenging agent, and/or chelating agent included as actives along with the skin lightening agent. The inclusion of two, three, or all four of these agents with the skin lightening agent increases the skin lightening benefits of the composition.

E. Retinoids

In a preferred composition useful in the subject invention, a retinoid, preferably retinoic acid, is included as an active along with the skin lightening agent. The inclusion of a retinoid increases the skin lightening benefits of the composition. A safe and effective amount of a retinoid may be added to the compositions useful in the subject invention, preferably about from 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereo isomers of these compounds, such as all-trans retinoic acid and 13-cis-retinoic acid.

In a preferred composition useful in the subject invention, compositions comprise one, any two, any three, any four, and/or five of a sunscreening agent, anti-inflammatory agent, anti-oxidant/radical scavenging agent, chelating agent, and/or a retinoid included as actives along with the skin lightening agent. The inclusion of two, three, four, or all five of these agents with the skin lightening agent increases the skin lightening benefits of the composition.

Methods for Lightening Skin in Mammals

The subject invention relates to methods for skin lightening in mammals. Such methods comprise the administration of a safe and effective amount of a skin lightening agent. The amount of active agent and frequency of application will vary widely depending upon the skin color already in existence in the subject, the rate of further darkening of the skin, and the level of lightening desired.

A safe and effective amount of skin lightening agent in a topical composition is applied, generally from about 1 g to about 10 g per $cm^2$ skin per application, preferably from about 2 g to about 8 $g/cm^2$ skin per application, more preferably from about 3 g to about 7 $g/cm^2$ skin, also preferably from about 4 g to about 5 $g/cm^2$ skin. Application preferably ranges from about four times a day to about twice a week, more preferably from about three times a day to about once every other day, more preferably still from about once daily to about twice daily. Application for at least five days is required to see a skin lightening effect in lower animals. Application for at least one month is required to see an effect in humans. After lightening is achieved, the frequency and dosage can be reduced to a maintenance level, as desired. Such maintenance varies according to the individual, but is preferably from about 1/10 to about 1/2, more preferably from about 1/5 to about 1/3 of the original dosage and/or frequency, as needed.

A preferred method of the subject invention for skin lightening in mammals involves applying both a safe and effective amount of the skin lightening agent and a safe and effective amount of one or more of a sunscreening agent, an anti-inflammatory agent, an anti-oxidant/radical scavenging agent, a chelating agent and/or a retinoid to the skin simultaneously. As used herein, "simultaneous application" or "simultaneously" means applying the agents to the skin at the same sites on the body at about the same time. Though this can be accomplished by applying the agents separately to the skin, preferably a composition comprising all the desired agents commingled is applied to the skin. The amount of sunscreening agent applied is preferably from about 0.01 mg to about 0.1 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of anti-oxidant/radical scavenging agent preferably applied is from about 0.01 mg to about 1.0 mg, more preferably from about 0.05 mg to about 0.5 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of retinoid applied is preferably from about 0.001 mg to about 0.5 mg per $cm^2$ skin, more preferably from about 0.005 mg to about 0.1 mg per $cm^2$ skin. The amount of skin lightening agent applied is preferably from about 0.001 mg to about 2 mg per $cm^2$ skin per application, more preferably from about 0.01 mg to about 1 mg per $cm^2$ skin per application.

Procedure for making a water-in-silicone gel composition of the present invention For example, a water-in-silicone gel composition of the present invention can be made by the following procedure.

(i) A compound of the formula (I) is dissolved in the average polarity solvents (active phase-I)

(ii) Water soluble ingredients are mixed together in a separate container (water phase)

(iii) After the two mixtures are clear, the water phase are mixed in the active phase-I and the mixture is stirred well. (active phase-2)

(iv) The active-phase-2 and a mixture of dimethicone copolyol surfactant and cyclomethicone are mixed slowly with constant stirring in a separate container to form a stable water-in-silicone gel composition of the present invention.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Test Example 1

Procedure for making control composition

THPOP is dissolved in polypropylene glycol (14) butyl ether (THPOP phase-1) Separately, polyoxyethylene (21) stearyl alcohol, polyoxyethylene (2) stearyl alcohol, cetyl alcohol, stearyl alcohol, cyclomethicone and ascorbyl palmitate are dissolved at 70 C. and stirred well. The THPOP phase-1 is added thereto and mixed continuously. (THPOP phase-2) In another vessel, all other ingredients than the above are dissolved at 70 C. (water phase) The THPOP phase-2 and the water phase are mixed well and allowed to cool to obtain oil-in-water emulsion (o/w emulsion). The components of control is shown in Table 1.

Procedure for making Test Composition No. 1

THPOP is dissolved in a mixture of diethylene glycol monoethyl ether, propylene glycol and ethanol. (THPOP phase-1) In a separate container, deionized water, sodium bisulfite, sodium sulfite, glycerin and benzyl alcohol are mixed. (water phase)

After the two mixtures are clear, the water phase are mixed in the THPOP phase-1 and the mixture are stirred well. (THPOP phase-2)

In a separate beaker, DC Q2-3225C and the THPOP phase-2 are mixed slowly with constant stirring.

A stable water-in-silicone gel is formed. The component of composition No. 1 is shown in Table 2.

TABLE 1

Control (Oil in Water emulsion)

| Component | Amount (weight %) |
|---|---|
| De-ionized water | 75.70 |
| Hydrochloric Acid 1N | 2.30 |
| Triethanolamine | 1.40 |
| Mg Ascorbic Phosphate | 0.10 |
| Sodium Metabisulfite | 0.05 |
| Disodium EDTA | 0.05 |
| Polyoxyethylene (21) stearyl alcohol (21) | 2.00 |
| Polyoxyethylene (2) stearyl alcohol (2) | 1.00 |
| Polypropylene glycol (14) Butyl Ether | 7.50 |
| Cetyl Alcohol | 3.00 |
| Stearyl Alcohol | 1.50 |
| Cyclomethicone | 1.00 |
| Ascorbyl Palmitate | 0.10 |
| THPOP | 3.00 |
| Butylene glycol | 1.00 |
| Glydant Plus | 0.30 |

("Glydant Plus" is Dimethylol-5,5-dimethylhydantoin (and) Iodopropynyl Butyl carbamate)

TABLE 2

Composition No. 1 (Water in Silicone gel)

| Component | Amount (weight %) |
|---|---|
| Deionized water | 30.20 |
| THPOP | 3.00 |
| Diethylene glycol monoethyl ether (transcutol) | 20.00 |
| Propylene glycol | 15.00 |
| Ethanol | 10.00 |
| Sodium Bisulfite(NaHSO3) | 0.20 |
| Sodium Sulfite (Na2SO3) | 0.50 |
| Benzyl alcohol | 0.60 |
| glycerin | 0.50 |
| DC Q2-3225C | 20.00 (2% Dimethicone copolyol and 18% Cyclomethicone) |

("DC Q2-3225C" is a mixture of 90% Cyclomethicone and 10% Dimethicone copolyol)

Test Method (1) Apparatus

The unjacketed diffusion cell is used. The corss-sectional area for penetration is 0.79 cm$^2$. This design is described by E. W. Merritt and E. R. Cooper, J. Controlled Release, 1(2), 161–162. Low glass tops that permit evaporation of the dose solution will be used for this study. The diffusion cells are maintained at body temperature of 37 C. in aluminum blocks which sit in a stirring heating module (Peirce Chemical Co.). Each aluminum block can accommodate six cells. The module controls the temperature and provides the stirring motor for the diffusion cells.

(2) Buffer Solution

The physiological saline solution used in this preparation is Dulbeco's phosphate buffered saline without calcium chloride and sodium bicarbonate (hereafter called "pbs") obtained from Wako Pure Chemical Industries LTD, CAM7276. Pbs is reconstituted with distilled water according to labeled instruction and 0.002% (s/v) sodium azide (Wako Pure Chemical Industries LTD, KCE 6293) is added to retard microbial growth. The pbs solution is maintained in a 37 C. water bath throughout the experiment in order to degas the solution. Evacuation of the solution using an aspirator, with stirring, for 15 minutes is also acceptable.

(3) Excised Human Cadaver Skin

Frozen excised human skin to a thickness of 0.25 mm (following washing and hair clipping) can be obatained from the Ohio Valley Skin and Tissue Center (Shriners Burns Institute, Cincinnati, Ohio). Skin is bathed in a solution of broad-spectrum antibiotics for 24 hours, treated with a 10% glycerol solution, wrapped in gauze, and placed in sealed sterile foil packs. The skin is cut into ~1.2×1.2 cm$^2$ using a scalpel (Keisei Medical industrial Co., handle #4, balde #21). The receptor compartments of the glass diffusion cells, filled with pbs solution (4–5 ml), are maintained at 37 C. in the aluminum blocks. The squares are mounted horizontally onto the cells with the sratum corneum facing the donor compartment and the dermis in contact with the receptor compartment. Non-occluded glass tops are placed onto the cells and firmly clamped in place. The aluminum blocks are placed back into the modules and micro magnetic stir bars are put into the receptor compartments of the cells to continually stir throughout the course of the experiment.

(4) Experimental Methods

The skin is allowed to equilibrate overnight, or for a minimum of 16 hours, with the dermis in contact with pbs solution and the stratum corneum exposed to air. A basic computer program is used to randomize the treatment groups and each diffusion cell is labeled accordingly. Following equilibration and just prior to dosing, the solution in the receptor compartment is discarded and refilled with fresh pbs solution. This procedure consists of pouring out the solution in the receptor compartment, rinsing with 2–3 ml of fresh pbs solution and refilling with fresh pbs solution. When pouring out solution, a gloved hand containing a magnet is used to prevent the micro stir bar from being expelled. Air bubbles which collect on the dermal surface of the skin are removed by holding the glass cell at an angle and gently tapping. Temperature of the solution in the receptor compartment is randomly observed, and adjusted if necessary, throughout the course of the experiment using a SATO PAC-9400 thermocouple thermometer.

(5) Dosing and Sampling Procedures

Test compositions and controls are dosed onto the stratum corneum (donor compartment) using a pipettor. If a small volume of material is dosed, the pipette tip is used to distribute the material evenly over the skin. If occlusion is called for, a small piece of parafilm is placed over the glass top immediately following dosing. Receptor compartment samples are usually collected 3, 6, 24 hours post-dose. Sampling consists of pouring the solution from the receptor compartment into a vial, risining with 2–3 ml of pbs solution and adding this rinse to the vial, then refilling with fresh pbs solutoin. Blank samples (pbs solution only) are obtained after each collection period and used for the background determination. Dummy dosing solution aliquots are weighed into scintillation vials for HPLC analysis in order to calculate the average dose aplied to each cell. Aliquots from a prepared solutio of test material and ethanol are also submitted for HPLC analysis to standardize the results and establish a conversion factor for the data analysis.

(6) Cleaning Procedures

At the end of the experiment, cells are dismantled and washed in a strong detergent solution (Alconox), rinsed with distilled water and allowed to air dry. Skin is wrapped in foil and stored in the freezer prior to disposal by incineration. In case of lacking incineration facility, a concentrated $H_2SO_4$ bath can be used to dissolve skin. Stir bars are rinsed and placed overnight in a beaker containing ethanol. Clamps are rinsed in distilled water and occasionally washed in an Alconox solution.

(7) HPLC Analysis

The penetration samples and aliquots of dosing and standard solutions are then analyzed for THPOP% by HPLC, (High Performance Liquid Chromatography-Shimazu LC-9A using JSPHERE ODS M80 Column)

Penetration value was calculated by the following equation.

Penetrated value(%)=penetrated amount of THPOP at each time point(mg)/amount of THPOP in applied composition(mg)×100

The test result is shown in Table 3.

TABLE 3

| | Penetration value (%) in each time | | |
|---|---|---|---|
| Tested composition | 3 hrs | 6 hrs | 24 hrs |
| Composition No. 1 | 2.6 | 6.8 | 39 |
| Control | 2.0 | 2.8 | 7.7 |

Test Example 2

The following example shows that the effect of enhanced penetration is not obtained by the solvent, but is obtained by the water-in-silicone gel formulation of the compound of formula (I).

Procedure for making Composition No. 2

THPOP is dissolved in diethylene glycol monoethyl ether. (THPOP phase-1) In a separate container, deionized water, sodium bisulfite, triethanolamine, glycerin, benzyl alcohol and sodium citrate are mixed. (water phase) After the two mixtures are clear, the water phase are mixed in THPOP phase-1 and stirred well. (THPOP phase-2)

In a separate beaker, DC Q2-3225C and the THPOP phase-2 are mixed slowly with constant stirring.

A stable water-in-silicone gel is formed.

The component of composition No. 2 is shown in Table 4.

Procedure for making comparative composition No. 1

THPOP is dissolved in diethylene glycol monoethyl ether (THPOP phase-1). In a separate container, deionized water, sodium bisulfite, triethanolamine and benzyl alcohol, sodium citrate and hydroxy ethyl cellulose are mixed (water phase). After the two mixtures are clear, the water phase are mixed in the THPOP phase and stirred well to obtain an aqueous gel. (This is not a water-in-silicone gel.) The component of comparative composition No. 1 is shown in Table 4.

TABLE 4

| Component | Composition No. 2 (water-in-silicone gel) amount (weight %) | Comparative composition No. 1 (Aqueous Gel) amount (weight %) |
|---|---|---|
| THPOP | 3.00 | 3.00 |
| Transcutol (diethylene glycol monoethyl ether) | 35.00 | 35.00 |
| Benzyl alcohol | 0.60 | 0.60 |
| Sodium bisulfite | 0.08 | 0.20 |
| Triethanolamine | 0.14 | 0.35 |
| Sodium Citrate | 0.31 | 0.80 |
| Glycerin | 3.00 | — |
| Hydroxy ethyl cellulose | — | 0.75 |
| DC Q2-3225C | 20.00 | — |
| | | (2% Dimethicone copolyol and 18% Cyclomethicone) |
| Deionized water | 37.87 | 59.30 |

("DC Q2-3225C" is a mixture of 90% Cyclomethicone and 10% Dimethicone copolyol)

Test Method

Test was conducted by the same method as the test method of Example 1.

The active penetration profiles for the above formulas are shown in Table 5:

TABLE 5

| | penetration value (%) in each time | | |
|---|---|---|---|
| Tested composition | 3 hrs | 6 hrs | 24 hrs |
| Composition No. 2 | 0.65 | 1.51 | 26.40 |
| Control (O/W Emulsion) (same as the control in Test Example 1) | 2.00 | 2.78 | 6.53 |
| Comparative composition No. 1 | 0.40 | 0.71 | 8.80 |
| Control (O/W emulsion) (same as the control in Test Example 1) | 1.19 | 2.19 | 8.90 |

What is claimed is:

1. A composition comprising:
   a) a safe and effective amount of a compound of the formula (I)

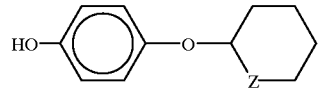

wherein Z is Oxygen or Sulfur,
   b) a mixture of dimethicone copolyol surfactant and cyclomethicone and,
   c) a cosmetically-acceptable carrier for said compound of formula (I) and said mixture;
   and wherein said composition is in the form of a water-in-silicone gel and is suitable for skin lightening.

2. The composition of claim 1 wherein Z is Oxygen.

3. The composition of claim 1 wherein Z is Sulfur.

4. The composition of claim 1 further comprising an average polarity solvent.

5. The composition of claim 1 further comprising water soluble glycol ether as an average polarity solvent.

6. The composition of claim 4 wherein said compound of the formula (I) is dissolved in said solvent.

7. The composition of claim 1 further comprising a solvent which has solubility parameter of 7 to 11.

8. The composition of claim 7 wherein said compound of the formula (I) is dissolved in said solvent.

9. The composition of claim 6 wherein said solvent is diethylene glycol monoethyl ether as an average polarity solvent.

10. The composition of claim 6 wherein said solvent is a combination of diethylene glycol monoethyl ether, ethanol and propylene glycol as an average polarity solvent.

11. The composition of claim 1 wherein the composition is a topical composition.

12. A gel composition which comprises the water-in-silicone gel composition according to claim 1.

13. A lotion composition which comprises the water-in-silicone gel composition according to claim 1.

14. An ointment composition which comprises the water-in-silicone gel composition according to claim 1.

15. A process for preparing a water-in-silicone gel composition comprising the steps of (i) dissolving a compound of the formula (I)

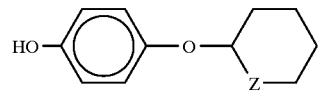

formula (I)

wherein Z is oxygen or sulfur, in an average polarity solvent to obtain the mixture 1;

(ii) mixing water-soluble ingredients together to obtain the mixture 2;

(iii) mixing the mixture 1 and the mixture 2 to obtain the mixture 3; and (iv) mixing the mixture 3 with a mixture of dimethicone copolyol surfactant and cyclomethicone.

16. A method for skin lightening in mammals which comprises topical application of the water-in-silicone gel composition according to claim 1.

* * * * *

UNITED STATES PATENT AND TRADEMARK OFFICE
CERTIFICATE OF CORRECTION

PATENT NO. : 6,258,344 B1
DATED : July 10, 2001
INVENTOR(S) : A. Venkateswaran

It is certified that error appears in the above-identified patent and that said Letters Patent is hereby corrected as shown below:

Column 2,
Line 67, "18:85" should read -- 15:85 --.

Column 3,
Line 48, "soluble ether" should read -- soluble glycol ether --.
Line 57, "give" should read -- given --.

Column 4,
Line 54, "ultraviolent" should read -- ultaviolet --.

Column 6,
Line 48, "given" should read -- not given --.

Column 11,
Line 53, "stirring heating" should read -- stirring-heating --.

Column 13,
Line 11, "Pentrated" should read -- Penetration --.

Signed and Sealed this

Twenty-ninth Day of January, 2002

Attest:

*Attesting Officer*

JAMES E. ROGAN
*Director of the United States Patent and Trademark Office*